United States Patent

Grace et al.

Patent Number: 5,556,374
Date of Patent: Sep. 17, 1996

[54] PATELLAR ALIGNMENT DEVICE

[76] Inventors: Kathleen J. Grace; Anne M. Fonte, both of 7182 Caminito Zabala, San Diego, Calif. 92122; John P. Buser, 837 Cornish Dr., San Diego, Calif. 92107

[21] Appl. No.: 317,755

[22] Filed: Oct. 4, 1994

[51] Int. Cl.⁶ .................. A61F 3/00; A61F 5/00; A61F 13/06
[52] U.S. Cl. .................. 602/26; 602/20; 602/23; 602/62
[58] Field of Search .................. 602/26, 60, 61, 602/62, 75, 20, 23; 606/201, 202, 203, 204; 2/2, 22, 24, 62

[56] References Cited

U.S. PATENT DOCUMENTS

| | | |
|---|---|---|
| D. 352,111 | 11/1994 | Watkins . |
| 563,468 | 7/1896 | Fergusson . |
| 2,377,339 | 6/1945 | Greene . |
| 3,214,501 | 10/1965 | Strauss .................. 602/75 X |
| 3,463,147 | 8/1969 | Stubbs .................. 602/26 |
| 4,084,584 | 4/1978 | Detty .................. 602/26 |
| 4,479,495 | 10/1984 | Isaacson .................. 606/204 |
| 4,534,364 | 8/1985 | Lamoreux . |
| 4,549,555 | 10/1985 | Fraser et al. . |
| 4,583,554 | 4/1986 | Mittelman et al. . |
| 4,649,934 | 3/1987 | Fraser et al. . |
| 4,700,698 | 10/1987 | Kleylein .................. 602/26 |
| 4,822,365 | 4/1989 | Walker et al. . |
| 4,969,471 | 11/1990 | Daniel et al. . |
| 5,156,163 | 10/1992 | Watkins et al. . |
| 5,267,951 | 12/1993 | Ishii .................. 602/26 |

FOREIGN PATENT DOCUMENTS

| | | | |
|---|---|---|---|
| 10389 | 4/1980 | European Pat. Off. .................. 602/26 |
| 329815 | 8/1989 | European Pat. Off. .................. 602/26 |
| 2553996 | 5/1985 | France .................. 602/26 |
| 9203110 | 5/1992 | WIPO .................. 602/26 |

*Primary Examiner*—Richard J. Apley
*Assistant Examiner*—Kim M. Lee

[57] ABSTRACT

A orthopaedic device for aligning the patella includes a patellar pad which is affixed to the leg of a patient over the patella. A sleeve having an aperture is placed on the leg to project the patellar pad through the aperture. The sleeve includes a gripper located a distance from the aperture. The device also includes an aligner. The aligner has an attachment that is connectable with the patellar pad through the aperture. Additionally, the aligner has at least one elastic strap connectable under tension to the gripper. By selectively attaching the elastic strap or straps between the patellar pad and the gripper, a force is generated of the proper magnitude and direction to align the patella. In alternative embodiment, the sleeve includes an activator positioned between the sleeve and the patient's vastus medialis oblique muscle. Contact between the activator and the vastus medialis oblique muscle allows the patient to isolate and selectively train that muscle and provides a stimulating therapeutic effect.

20 Claims, 3 Drawing Sheets

PATELLAR ALIGNMENT DEVICE

FIELD OF THE INVENTION

The present invention relates generally to orthopaedic braces. More particularly, the present invention relates to orthopaedic braces used to stabilize and correct the biomechanical alignment of the knee. The present invention is particularly, but not exclusively, useful as a means of correctly aligning the patella and biomechanically stimulating muscle contraction thereby reducing or eliminating pathological conditions of the patellofemoral joint associated with patella malalignment.

BACKGROUND OF THE INVENTION

Pain in the patellofemoral joint, or pain in and around the kneecap, is a frequent and increasingly common problem and is particularly troublesome for athletes and young women. Typically, patellofemoral joint pain is dull and aching in character and is generally localized around the patella. Chronic patellofemoral joint pain may also lead to other maladies including tendinitis of the patellar tendon, muscle atrophy and joint arthritis.

One type of patellofemoral joint pain is associated with malalignment of the patella with respect to the trochlear notch in the femur. For instance, the patella may encroach too closely on either the medial or lateral sides of the trochlear notch. A malalignment of this type is referred to as a glide. A similar malalignment occurs when the patella tilts or leans towards the medial or lateral sides of the trochlear notch. In this case the malalignment is referred to as a tilt. A third malalignment type, known as a rotation, occurs when the long axis of the patella fails to follow the long axis of the femur. Finally, anteroposterior malalignment occurs when the inferior pole of the patella is tilted posteriorly when compared to the superior pole. In general, a given patient may exhibit one or more of the four malalignment types within a single knee. Diagnosis and treatment is further complicated by the possibility that a given malalignment may have a different static and dynamic configuration.

Several methods have been developed to treat patellar malalignment. Perhaps the most effective treatment has been the employment of various physical therapy programs designed to stretch the hamstring muscles and increase the strength of the quadriceps muscles. In particular, exercises which strengthen the vastus medialis oblique muscle have been found to be beneficial in correcting patellar malalignment. In practice, however, it has been found that patients often find it difficult to selectively exercise the vastus medialis oblique muscle making the process of increasing the strength of this muscle particularly difficult.

Another treatment method in common use is the employment of a neoprene sleeve shaped to be slipped over the patient's foot and worn over the effected knee. Sleeves of this type often feature an opening for the patient's patella and are generally constructed of ⅛-inch or ¼-inch neoprene rubber with a nylon outer and inner covering. In use, the neoprene sleeve fits over the patient's knee and reduces excessive lateral (outside) motion of the patella. Use of neoprene sleeves has been found to be effective for treating patella malalignment in a very limited number of cases. The inability of the standard neoprene sleeve to provide an adequate alignment force, however, has limited the effectiveness of the sleeve in most malalignment cases.

A sleeve system which attempts to overcome the inability of the standard sleeve to generate a sufficient aligning force is disclosed in U.S. Pat. No. 4,296,744 which issued to Palumbo for an invention entitled "Dynamic Patellar Brace." The Palumbo device includes the use of a neoprene sleeve with an aperture or hole for location of the patella. In addition, the Palumbo device includes a bracing pad located by a set of straps. In use, the bracing pad is positioned against one side of the patella and the straps are used to pull the patella into alignment.

Although the Palumbo device may be used to create a greater aligning force than would be attainable by the use of a standard sleeve, there are still doubts as to whether the force produced is great enough and particularly whether the aligning force will remain constant as the patient exercises. In greater detail, it may be appreciated that the aligning force used in the Palumbo device is limited by the ability of the bracing pad to apply force to the patella. Since the bracing pad is held in place only by the interaction of the pad material against the skin of the patient, the ability of the bracing pad to align the patella is necessarily limited. Additionally, it may be appreciated that there will be a natural tendency for the bracing pad to slip over the patella during the course of exercise limiting the effectiveness of the bracing pad still further.

A treatment method that overcomes the disadvantages of the Palumbo device is the use of patellofemoral taping, commonly known as the "McConnell Taping Technique." The McConnell Technique applies a series of adhesive tape strips to the patient's knee. The tape strips cross over the patient's patella and wrap around to the back of the knee. By applying the tape strips under tension, a relatively large force may be applied to align the patient's patella. Additionally, the tape strips may be individually aligned for each patient to account for the various malalignment components present in a particular knee. In general, the McConnell Technique has been found to be highly effective at treating a number of different and varying patellar malalignments. The McConnell Technique, however, is subject to a number of disadvantages. In particular, the McConnell Technique is relatively inflexible after the tape has been first applied. In particular, once the series of tapes have been applied to the patient's knee, there is no provision that allows the tapes or the tension in a particular tape to be adjusted to improve effectiveness of the procedure or to correct a mistake in the original application.

Additionally, experience has demonstrated that application of the taping system prescribed by the McConnell Technique is a time consuming process, particularly when performed by the patient. Even when the tapes are correctly applied, there is a possibility that the tapes will become subsequently dislodged, particularly in the case of prolonged exercise and particularly at the point of attachment of the tape with the back of the knee where the tapes are subject to the greatest amount of dynamic stress.

In light of the above, it is an object of the present invention to provide a patellar alignment system that provides an alignment force that is adequate to align a wide range of patellar malalignments. It is another object of the present invention to provide a patellar alignment system that provides an alignment system that may be easily tailorable to individual patients. It is yet another object of the present invention to provide a patellar alignment system that may be easily applied and easily adjusted after application. It is still another object of the present invention to provide a patellar alignment system that is stable even under the rigors present during intense exercise. It is yet another object of the present invention to provide a patellar alignment system that is cost effective to manufacture and relatively simple to operate.

SUMMARY OF THE INVENTION

According to the present invention, an orthopaedic device for aligning the patella into a proper anatomical orientation includes a patellar pad which can be affixed to the leg over the patella, a sleeve with a gripper which can be placed on the leg to distance the gripper from the patellar pad, and an aligner which is connectable to both the pad and the gripper to create an aligning force on the patella.

The patellar pad of the present invention includes a patellar connector mounted to a flat flexible substrate. The substrate has an adhesive backing on the surface that is opposite to the patellar connector. In order to stabilize and provide added reinforcement for the connector on the substrate, the connector may be stitched onto the substrate. Preferably, when mounted on the substrate, the exposed portion of the connector has the loops or hooks that are common to VELCRO (VELCRO is a trademark of VELCRO USA Inc.) fasteners.

The sleeve of the present invention is made of a flexible, elastic material and has a substantially hollow cylindrical shape which allows the sleeve to be positioned over the leg. Further, the sleeve is formed with an aperture which is dimensioned to permit projection of the patellar connector through the aperture. The gripper is fastened to the outer surface of the sleeve at a distance from the aperture and, like the patellar connector, the exposed portion of the gripper preferably has the loops or hooks that are common to VELCRO fasteners.

For the present invention, the aligner has a first attachment which is connectable with the patellar connector of the patellar pad and at least one second attachment which is connectable with the gripper. More specifically, and preferably, the aligner has a plurality of elastic straps which extend from the first attachment, each of which support a second attachment that is individually engageable with the gripper. To accomplish the connections with the gripper on the sleeve and the patellar pad affixed to the patient's leg, the first and second attachments of the aligner preferably have velcro type fasteners which are compatible with the respective fasteners on the gripper and on the patellar connector. Further, the gripper is of a sufficient size to allow for the selective placement of the individual second attachments on the gripper.

In the operation of the present invention, the adhesive surface of the patellar pad substrate is placed on the leg to affix the patellar pad in a location over the patella. The patient's leg, with patellar pad attached, is inserted into the sleeve and the sleeve is positioned on the leg to project the patellar connector through the aperture of the sleeve. The first attachment of the aligner is then attached to the patellar connector. With the aligner attached to the patellar connector, the user is then free to pull on the elastic straps of the aligner, and to selectively locate attachment points for the second attachments on the gripper creating an aligning force on the patellar connector. As intended for the present invention, the aligning force created on the patella will have an appropriate magnitude and direction to effectively eliminate glide, tilt, rotation and anteroposterior malalignments and correctly align the patella into a proper anatomical orientation.

In an alternative embodiment of the present invention, an activator is attached to the inside of the sleeve to contact the patient's vastus medialis oblique muscle. The activator consists of a blunt probe and an attachment means. Operationally, the probe is designed to function as a means whereby the patient may positively isolate and exercise the vastus medialis oblique. Additionally, the interaction between the probe and the sleeve provides manual stimulation to the vastus medialis oblique muscle with an associated therapeutic effect.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts.

DESCRIPTION OF THE PREFERRED EMBODIMENTS

Figure 1:
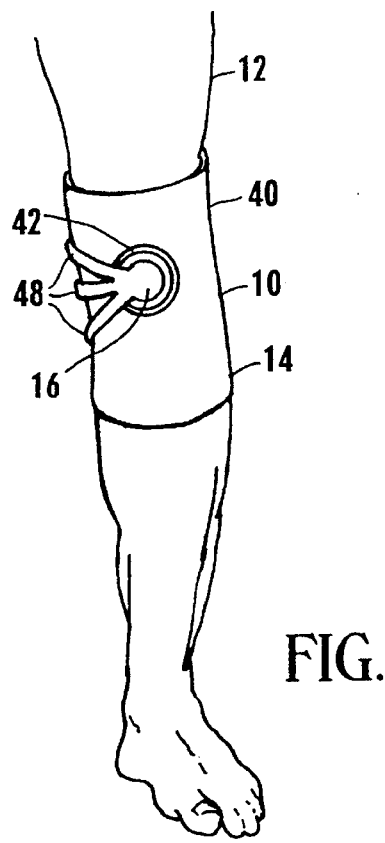
FIG. 1 is a perspective view of the patellar alignment device of the present invention operationally positioned over a human leg and knee and shown from a forward and medial point of reference.

The present invention is a device and a method for aligning the patella of the human knee into a proper anatomical orientation. The general relationship between the elements of the present invention and a patient's leg are shown in FIG. 1 where the patellar alignment device 10 is shown operationally positioned on a human leg 12. In particular, it may be seen that the patellar alignment device 10 includes a sleeve 14 and an aligner 16.

Figure 2:
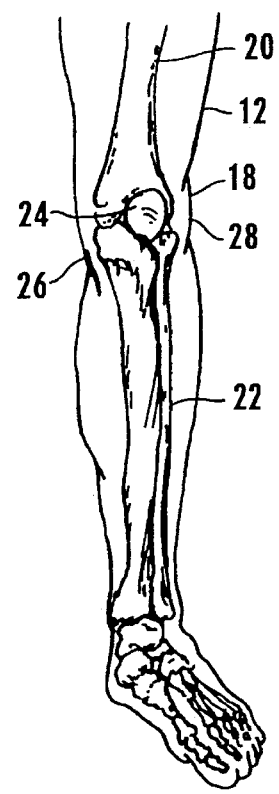
FIG. 2 is anatomical depiction of the major bone structure of a human leg.

The use of the present invention may be better understood by first referring to FIG. 2 where the anatomical components of the human leg 12 are shown. FIG. 2 shows that the human knee 18 comprises a hinged joint between the femur 20 and the tibia 22. As shown in FIG. 2, the patella 24 is located in front of the hinged joint connecting the femur 20 and the tibia 22. In general, the patella 24 serves as a fulcrum for tendons connecting muscles in the upper and lower leg (not shown).

It may be appreciated that the patella 24 is not fixed in location with respect to the knee 18. Instead, in proper anatomical motion, the patella 24 slides up and down in a line that generally parallels the major axis of the femur 20.

It may also be appreciated that failure of the patella 24 to maintain the required alignment with the knee 18 and the trochlear notch located in front of the femur 22 may result in incorrect function of the knee 18 and irritation to the patella 24 and other knee structures. In particular, if the patella 24 operates too closely to the medial side 26 of the knee 18 or too closely to the lateral side 28 of the knee 18, a glide malalignment exists and irritation may result. The same difficulties may arise if the patella 24 tilts towards the medial side 26 or the lateral side 28 of the knee 18. In addition, the patella 24 may be rotated with respect to the major axis of the femur 20 once again with resulting irritation. Irritation and other joint maladies may also occur if the inferior pole of the patella 24 is tilted posteriorly when compared with the superior pole of the patella 24.

Figure 3:
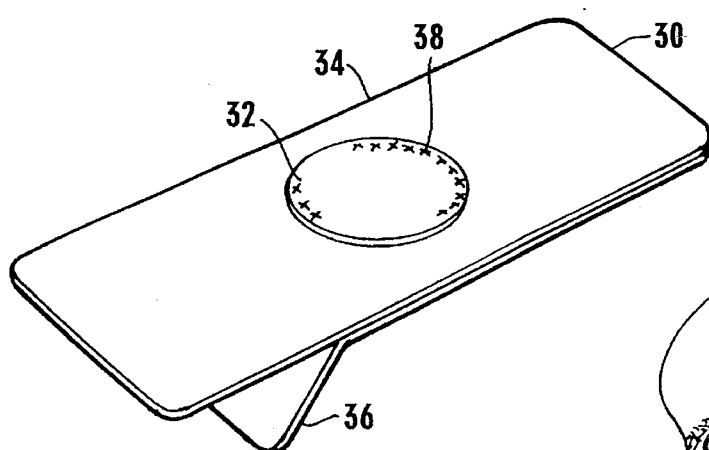
FIG. 3 is an isometric view of the patellar pad of the present invention.
Figure 4:
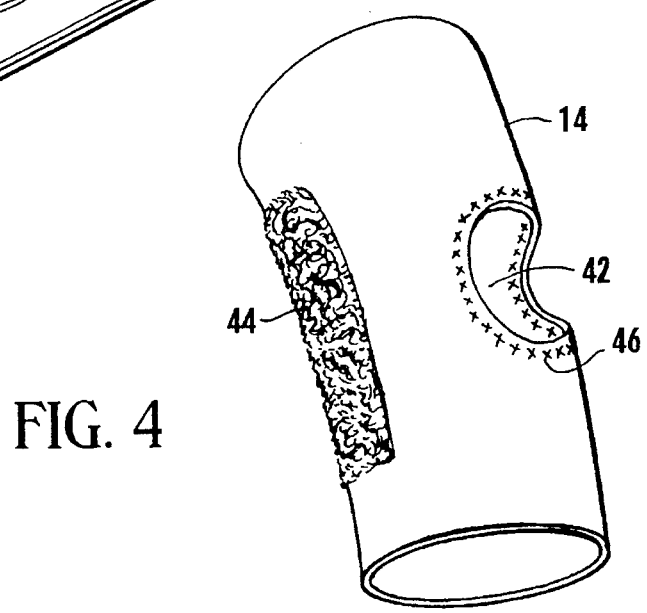
FIG. 4 is an isometric view of the sleeve of the present invention.
Figure 5:
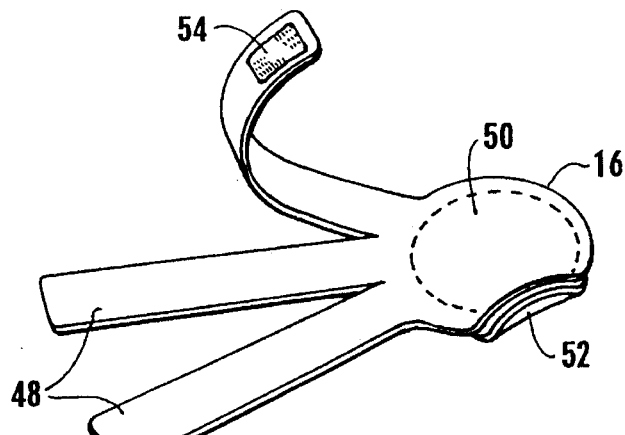
FIG. 5 is an isometric view of the aligner of the present invention.

To correct patellar alignment, the present invention provides a system of three basic components shown in FIGS. 3, 4 and 5. The first of these components, the patellar pad, is shown in FIG. 3 and generally designated 30. In FIG. 3, it can be seen that the patellar pad 30 includes a patellar connector 32 mounted to the front side of a flat rectangular substrate 34. The back side of the substrate 34 includes an adhesive coating (not shown) protected by a peel-off backing 36. It may be appreciated that the substrate 34 is constructed of compliant materials that are able to closely follow the contours of the human knee. Several types of commercially available medical adhesive tapes, such as HYPAFIX Tape manufactured by Smith and Nephew Donjoy Inc., are particularly suitable for this purpose. These tapes may be used alone or in laminated combinations to provide the desired combination of strength and flexibility.

It may also be appreciated that the patellar connector 32 may be preferably constructed as a circular velcro patch although other attachment devices are practical. In cases where VELCRO is used, however, reinforcing stitching 38 may be added to ensure that the patellar connector 32 does not separate from the patellar pad 30.

The second major component, the sleeve, is shown in FIG. 4 and generally designated 14. In greater detail, it can be seen that the sleeve 14 is a tube shaped structure which includes a hole or aperture 42 near the midpoint of the tube. In operation, the sleeve 14 is designed to slipped over the patient's knee and the aperture 42 is aligned over the patient's patella.

Diametrically opposed to the aperture 42, is a gripper 44. Operationally, the gripper 44 functions as an area of attachment for the aligner 16 shown in FIG. 1. As such, the gripper 44 may be fabricated from any material that provides a large area of attachment and which allows the sleeve 14 to accommodate the motion of the knee 18. Continuous loop VELCRO has been found to be suitable for this purpose. In addition, it has been found to be particularly efficient to implement the gripper 44 by providing a nylon cover to the sleeve 14 which includes an unbroken loop region suitable for anchoring hook type velcro connectors as well known in the pertinent art.

Preferably, the sleeve 14 is constructed of neoprene rubber. To increase the comfort of the patient, the sleeve 14 may be fabricated from multiple neoprene segments, enhancing the ability of sleeve 14 to adhere to the anatomical features of the patient's leg 12 and knee 18.

Additionally, the sleeve 14 may be fabricated with outer and inner layers of nylon to further enhance the patient's comfort and to provide additional durability. Durability is further enhanced by including a row of reinforcing stitching 46 along the periphery of the aperture 42.

The third component of the present invention, the aligner, is shown in FIG. 5 and generally designated 16. The structure of the aligner 16 consists of a plurality of elastic straps 48 connected to an aligner body 50. It may be appreciated that the aligner 16 is intended to be stretched between the patellar connector 32 and the gripper 44. To that end, the aligner body 50 includes a first connector 52 attachable with the patellar connector 32. In a similar fashion, each elastic strap 48 includes a second connector 54 attachable with the gripper 44.

Preferably, the aligner body 50 and elastic straps 48 are fabricated from a single piece of elastic material such as neoprene rubber. Additionally, the first connector 52 and second connector 54 are chosen to be compatible with the patellar connector 32 and the gripper 44 and will generally be fabricated as VELCRO type fasteners.

Figure 8:
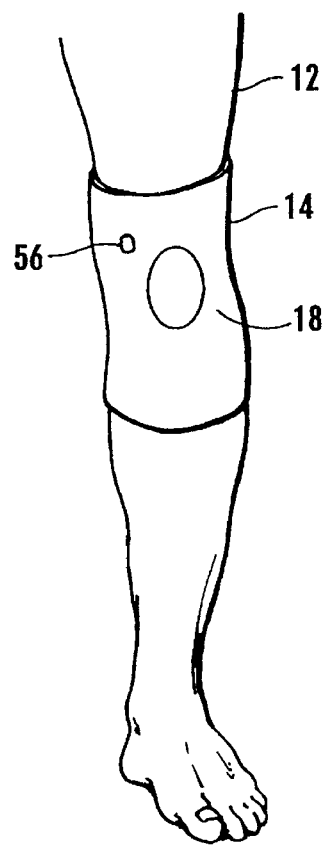
FIG. 8 is a perspective view of the activator of the present invention operationally positioned over a human leg and knee and shown from a forward and medial point of reference.

In an alternative embodiment of the present invention, an activator 56 is attached to the sleeve 14. The use of the activator 56 in cooperation with the sleeve 14 is shown in FIG. 8 where the combination of the sleeve 14 and activator 56 is shown operationally positioned over the patient's knee 18. It may be appreciated from FIG. 8 that correct positioning of the activator 56 locates the activator 56 over the patient's vastus medialis oblique muscle.

Figure 9:
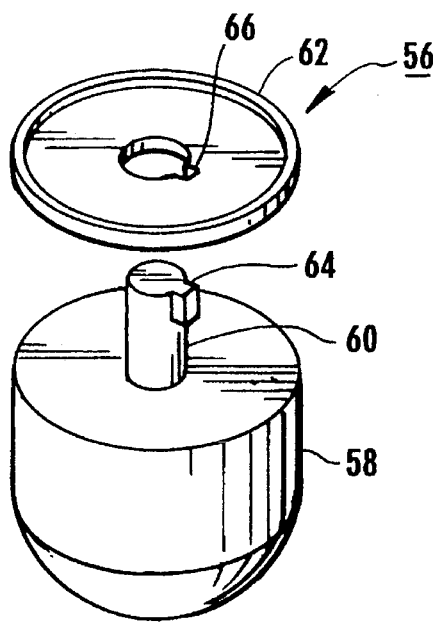
FIG. 9 is an isometric view of the activator of the present invention shown exploded for clarity.

The structural details of the activator 56 are shown in greater detail in FIG. 9 where it may be seen that the activator 56 includes a probe 58 attached to a post 60. The post 60 is designed to selectively attachable to a retainer 62. The selective attachment is accomplished by a key 64 included on the post 60 and a passageway 66 included in the retainer 62. The combination of the post 60 and retainer 62 allows the activator 56 to be attached to the sleeve 14 over the vastus medialis oblique muscle.

Figure 10:
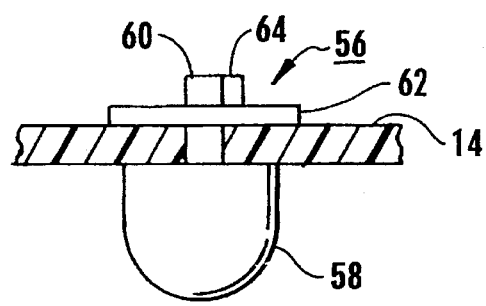
FIG. 10 is a side elevational view of the activator of the present invention.

Attachment of the activator 56 to the sleeve 14 is shown in greater detail in FIG. 10 where it can be seen that the post 60 is inserted through the sleeve 14. Once the post 60 is inserted through the sleeve 14, the retainer 62 is engaged with the post 60 by aligning the key 64 and the passageway 66. The retainer 62 may then be locked in to position by rotating the retainer 62 around the post 60 so that the passageway 66 is no longer aligned with the key 64. The combination of the post 60 and the retainer 62 is only one possible way in which the activator 56 may be attached to the sleeve 14. In general, any fastening method which securely attaches the activator 56 to the sleeve 14 and allows for easy attachment and detachment may be employed.

Operationally, it may be appreciated that the contact of the probe 58 with the patient's vastus medialis oblique muscle performs several functions. One function provided by the probe 58 is to positively identify the location of the vastus medialis oblique muscle to the patient allowing the patient to isolate and target the vastus medialis oblique muscle during strength training exercises. To perform this function, the probe 58 working with the sleeve 14 applies pressure to the patient's vastus medialis oblique muscle. The pressure applied by the probe 58 allows the patient to tactilely locate the vastus medialis oblique muscle and to sense when a particular exercise has caused the vastus medialis oblique muscle to become contracted. The patient may then modify and optimize exercises to have the greatest effect on the vastus medialis oblique muscle.

A second function provided by the probe 58 is manual stimulation of the patient's vastus medialis oblique muscle. Alternatively stated, it may be appreciated that the contact of the probe 58 with the vastus medialis oblique muscle will provide a stimulating action as the patient exercises and the vastus medialis oblique muscle moves in relation to the probe 58 and the sleeve 14. The stimulation associated with the use of the activator 56 enhances the patient's ability to strengthen the vastus medialis oblique muscle.

Figure 11:
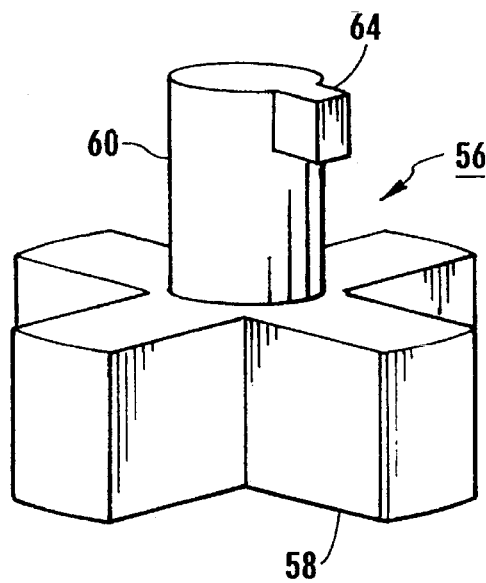
FIG. 11 is an isometric view of an alternative embodiment of the activator of the present invention.

To achieve the objectives of the present invention, it may be appreciated that different shapes may be employed for the probe 58. In particular, it may be appreciated that a blunt bullet-shape may be appropriate for probe 58. This configuration in shown in FIG. 9. Alternatively, it may be appreciated that more complex shapes may be desirable. FIG. 11 shows an alternative embodiment for the probe 58 where the blunt bullet shape of FIG. 9 has been replaced with a cross or tee shape. In general, the actual shape chosen for the probe 58 may be varied to adjust the amount of tactile feedback and stimulation provided by the activator 56.

OPERATION

Figure 6:
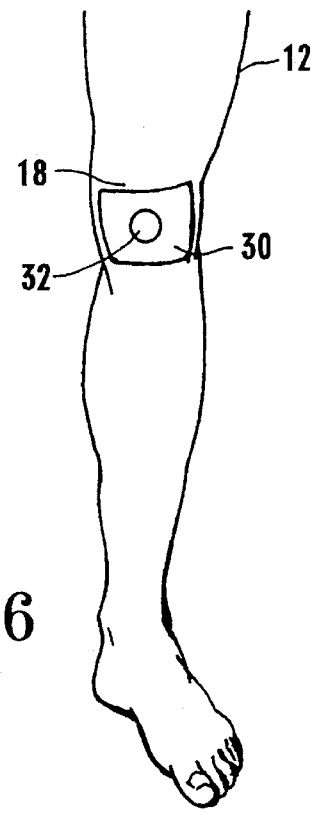
FIG. 6 is a perspective view of the patellar pad of the present invention operationally positioned over a human leg and knee shown from a forward and medial point of reference.

Application of the present invention begins by placement of the patellar pad 30 and patellar connector 32 over the patient's patella 24 as shown in FIG. 6. In greater detail, the peel-off backing 36 is first removed from the patellar pad 30. Once the peel-off backing 36 is removed, the patellar pad 30 is placed over the patella 24 and pressed into place. The pressure sensitive adhesive on the back of the patellar pad 30 forms a bond with the patient's knee 18 holding the patellar pad 30 and patellar connector 32 securely in place.

Figure 7:
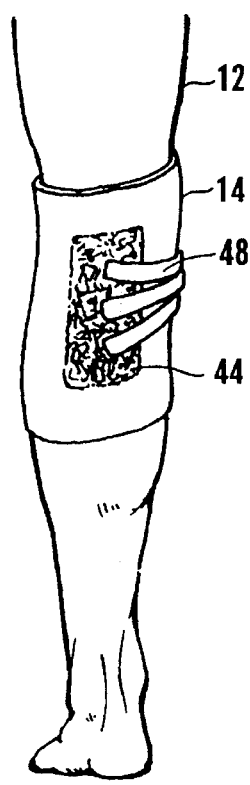
FIG. 7 shows the patellar alignment device of the present invention shown in FIG. 1 now shown from an anterior and lateral point of reference.

Referring now to FIG. 1, it can be seen that placement of the patellar pad 30 is followed by passing the sleeve 14 over the patient's foot and around the patient's knee 18 with the patient's patella 24 aligned with the aperture 42. In this configuration, it may be appreciated that the patellar connector 32 will protrude or project from the aperture 42 in the sleeve 14. It may also be appreciated that the gripper 44 mounted on the sleeve 14 will be positioned along the back of the patient's knee 18. The position of the gripper 44 with respect to the back of the knee 18 is easily seen in FIG. 7.

Referring again to FIG. 1, it can be seen that the final step in application of the patellar alignment device 10 is the attachment of the aligner 16. To attach the aligner 16, the first connector 52 is attached to the patellar connector 32 included in the patellar pad 30. In cases where velcro is used to implement the patellar connector 32 and first connector 52, attachment of the aligner 16 is simply a matter of placing the first connector 52 firmly in contact with patellar connector 32 through the aperture 42.

Once the aligner 16 is connected to the patellar pad 30, each of the elastic straps 48 is passed around the medial side 26 of the knee 18 and connected under tension to the gripper 44. In cases where the gripper 44 and the second connector 54 are implemented as VELCRO fasteners, attachment of the elastic straps 48 is simply a matter of bringing each of the elastic straps 48 into contact with the back of the sleeve 14 thereby bringing the second connector 54 into contact with the gripper 44.

It may be appreciated that the gripper 44 is intended to provide a number of possible points of attachment for each of the elastic straps 48. By providing a number of possible points of attachment, the force applied to the patella may be adjusted to fit the needs of the individual patient. Specifically, the magnitude and the direction of the force applied by each elastic strap may be varied to create the correct force required to properly align the patient's patella. It may also be appreciated that the number of elastic straps 48 employed may vary depending on the actual condition sought to be addressed by a particular implementation. Additionally, while the elastic straps 48 of the present invention will typically be deployed over the medial side of 26 of the patient's knee 18 there may be cases where it is advantageous to reverse the orientation of the aligner 16 to deploy the elastic straps 48 over the lateral side 28 of the knee 18.

While the particular orthopaedic device as herein shown and disclosed in detail is fully capable of obtaining the objects and providing the advantages herein before stated, it is to be understood that they are merely illustrative of the presently preferred embodiments of the invention and that no limitations are intended to the details of construction or design herein shown other than as described in the appended claims.

We claim:

1. An orthopaedic device for aligning the patella into a proper anatomical orientation which comprises:
   a pad fixedly adhereable to the leg of a patient to position said pad over the patella;
   a sleeve formed with an aperture, a leg of the patient being insertable into said sleeve to project said pad through said aperture;
   a gripper fastened to said sleeve; and
   an aligner having a first attachment and at least one second attachment, said first attachment being attachable to said pad and said second attachment being attachable in a selectable location on said gripper to generate a selectively orientable force on said pad for aligning the patella.

2. A device as recited in claim 1 further comprising a flexible substrate having a first side and a second side, said pad being positioned on said first side of said substrate and an adhesive being placed on said second side to adhere said second side of said substrate to the leg of a patient.

3. A device as recited in claim 1 further comprising:
   an activator with a probe, said activator engageable with said sleeve to position said probe between said sleeve and said vastus medialis oblique; and
   means attachable to said activator to retain said activator in attachment with said sleeve.

4. A device as recited in claim 2 further comprising a stitching between said pad and said substrate for reinforcing the positioning of said pad on said first side of said substrate.

5. A device as recited in claim 1 wherein said aperture is defined by a periphery, and said sleeve further comprises a reinforcing stitching surrounding said aperture near said periphery.

6. A device as recited in claim 1 wherein said sleeve is substantially cylindrical in shape and has an inner surface which is positioned against the leg of the patient and an outer surface.

7. A device as recited in claim 6 wherein said gripper is fastened to said outer surface of said sleeve, and said gripper is distanced from said aperture.

8. A device as recited in claim 1 wherein said first attachment of said aligner substantially conforms to said pad.

9. A device as recited in claim 8 wherein said aligner comprises a plurality of second attachments, each said second attachment being integral with said first attachment and extending therefrom.

10. A device as recited in claim 9 wherein said first attachment and said pad have respectively cooperating hooks and loops for making said attachment therebetween and said second attachments and said gripper have respectively cooperating hooks and loops for making said attachment therebetween.

11. A device as recited in claim 1 wherein said sleeve and said aligner are constructed from neoprene rubber.

12. An orthopedic device for aligning the patella into a proper anatomical orientation which comprises:

means adherable over the patella of a patient for establishing a first attachment point over the patella;

a sleeve formed with an aperture, a leg of the patient being insertable into said sleeve to project said first attachment point through said aperture;

means for establishing a second attachment point to said sleeve, said second attachment point being distanced from said first attachment point; and means simultaneously attachable to said first attachment point and to said second attachment point for applying a selectively orientable force to said first attachment point to align the patella.

13. A device as recited in claim 12 further comprising:

an activator with a probe, said activator engageable with said sleeve to position said probe between said sleeve and said vastus medialis oblique; and means attachable to said activator to retain said activator in attachment with said sleeve.

14. A device as recited in claim 12 wherein said means for establishing said first attachment point comprises:

a flexible substrate having a first side and a second side;

a pad affixed to said first side of said substrate; and an adhesive placed on said second side of said substrate to adhere said second side of said substrate to the leg of a patient with said pad over the patella.

15. A device as recited in claim 14 wherein said means for establishing said second attachment point comprises:

a sleeve formed with an aperture, said sleeve being substantially cylindrical in shape and having an inner surface which is positionable against the leg of the patient to project said pad through said aperture, and said sleeve having an outer surface; and a gripper fastened to said outer surface of said sleeve, said gripper being distanced from said aperture.

16. A device as recited in claim 15 wherein said means simultaneously attachable to said first attachment point and to said second attachment point is an aligner having a first attachment and at least one second attachment, said first attachment being attachable to said pad and said second attachment being attachable in a selective location on said gripper to pull on said pad for aligning the patella.

17. A device as recited in claim 16 further comprising a stitching between said pad and said substrate for reinforcing the positioning of said pad on said first side of said substrate, and wherein said aperture is defined by a periphery, and said sleeve further comprises a reinforcing stitching surrounding said aperture near said periphery.

18. A device as recited in claim 17 wherein said first attachment and said pad have respectively cooperating hooks and loops for making said attachment therebetween and said second attachments and said gripper have respectively cooperating hooks and loops for making said attachment therebetween.

19. A device as recited in claim 18 wherein said sleeve and said aligner are constructed from neoprene rubber.

20. A method for aligning the patella into a proper anatomical orientation which comprises the steps of:

affixing a flexible substrate to the leg of a patient, said flexible substrate having a first side and a second side with a pad being positioned on said first side of said substrate and an adhesive being placed on said second side thereof to adhere said second side of said substrate to the leg of a patient and position said pad over the patella; inserting the leg of the patient into a substantially cylindrical shaped sleeve, formed with an aperture, to project said pad through said aperture, said sleeve having an inner surface positioned against the leg of the patient and an outer surface, said sleeve further have a gripper fastened to said outer surface of said sleeve at a distance from said aperture; and simultaneously attaching an aligner to said pad and to a selectable location on said gripper to create a selectively orientable force on the patella for aligning the patella in a proper anatomical orientation.

* * * * *